United States Patent

Batorewicz

[11] 4,341,721
[45] Jul. 27, 1982

[54] DIPHOSPHITES

[75] Inventor: Wadim Batorewicz, New Haven, Conn.

[73] Assignee: Uniroyal, Inc., New York, N.Y.

[21] Appl. No.: 193,220

[22] Filed: Oct. 1, 1980

[51] Int. Cl.³ .......................... C07F 9/141; C08K 5/52
[52] U.S. Cl. ...................................... 260/930; 524/128
[58] Field of Search ........................................ 260/930

[56] References Cited

U.S. PATENT DOCUMENTS

| | | | |
|---|---|---|---|
| 3,240,704 | 3/1966 | Nelson et al. | 260/930 |
| 3,467,737 | 9/1969 | Brindell | 260/953 |
| 3,532,669 | 10/1970 | Hunter | 260/45.95 |
| 3,533,989 | 10/1970 | Wescott | 260/45.7 |
| 3,655,718 | 4/1972 | Schutze et al. | 260/930 |
| 3,694,395 | 9/1972 | Bain et al. | 260/930 |
| 4,134,876 | 1/1979 | Horner et al. | 260/930 |
| 4,187,212 | 2/1980 | Zinke et al. | 260/45.8 NT |

OTHER PUBLICATIONS

Mukmeneva et al., "Chem. Abs.", vol. 60, 5375d.

*Primary Examiner*—Anton H. Sutto
*Attorney, Agent, or Firm*—Marvin Bressler

[57] ABSTRACT

Diphosphites having the structural formula:

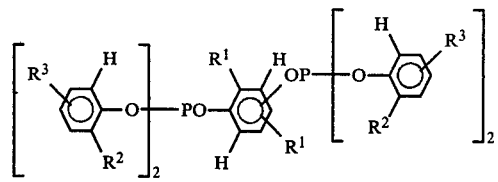

wherein:
$R^1$ and $R^2$ may be the same or different and are $C_4$ to $C_{12}$ tertiary alkyl or $C_9$ to $C_{14}$ tertiary aralkyl;
$R^3$ is hydrogen, $C_1$ to $C_{18}$ alkyl or $C_7$ to $C_{18}$ aralkyl. These hydrolytically stable solid diphosphites are useful as antioxidants in organic polymers such as polypropylene.

12 Claims, No Drawings

DIPHOSPHITES

This invention relates to hydrolytically stable diphosphites and their use as antioxidants in organic polymers.

The invention is concerned with hydrolytically stable solid diphosphites having the structural formula:

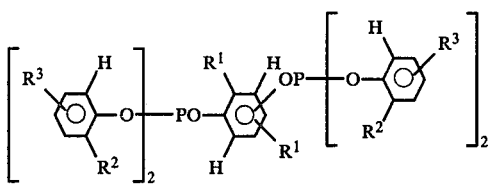

wherein $R^1$ and $R^2$ may be the same or different and are $C_4$ to $C_{12}$ tertiary alkyl or $C_9$ to $C_{14}$ tertiary aralkyl; $R^3$ is hydrogen, $C_1$ to $C_{18}$ alkyl or $C_7$ to $C_{18}$ aralkyl.

The term "tertiary aralkyl" means any aralkyl group within the scope of this invention having a tertiary radical position such as phenylisopropyl-2, 1,1-dimethyl-2-phenylethyl-1, 1,1-dimethyl-3-phenylpropyl-1 etc.

These solid phosphites are hydrolytically stable and melt in the 60°-100° C. range. They are easily processed during manufacture and do not cake under normal storage conditions. The new phosphites are very useful as antioxidants for organic polymers especially as processing aids for polyolefins.

References of Interest

1. CA 60, 5375d, N. A. Mukmeneva et al, describes preparation of tetraphenyl -1,4-(2,5-di-t-butylphenylene) diphosphite. This diphosphite is hydrolytically unstable.

2. U.S. Pat. No. 3,467,737, Sept. 16, 1969, and U.S. Pat. No. 3,532,669, Oct. 6, 1970 (Brindell), disclose phosphites based on 2,5-disubstituted hydroquinone and $PCl_3$ which contain free phenolic OH groups. The compounds of the present invention do not contain free OH groups. In addition, the present phosphites are prepared from three components and not two as described in the reference.

3. U.S. Pat. No. 4,187,212, Feb. 5, 1980 (Zinke et al), describes tris(2,4-di-t-butylphenyl) phosphite as a stabilizer for polyolefins. This phosphite is hydrolytically stable but it is not as effective as the compounds of the present invention as antioxidants.

4. U.S. Pat. No. 3,533,989, Oct. 13, 1970 (Wescott, Jr.), describes tris(2-t-butyl-4-methylphenyl)phosphite and tris(2-t-butyl-6-chloro-4-methylphenyl) phosphite as processing stabilizers for polyolefins. These are hydrolytically stable compounds, however, they are very similar to tris(2,4-di-t-butylphenyl)phosphite and are less effective than the compounds of the present invention.

DESCRIPTION OF THE INVENTION

Use of certain phosphites as antioxidants generally and as processing aids for polyolefins is well known in the art. One of the most widely used solid phosphites today in polyolefins is distearylpentaerylthritol diphosphite. This material is very difficult to handle because it is very sensitive to moisture. In addition, due to its low melting point (40°-50° C.), distearylpentaerythritol diphosphite, powder or flakes, tends to fuse on storage.

No such disadvantages are encountered with the phosphites of the present invention. These materials are very stable hydrolytically. Table I summarizes hydrolysis data obtained from a test consisting of stirring one (1) gram of the solid phosphite in 150 ml of distilled water at room temperature. The test measures the time required for the liquid phase to reach a pH of about four, indicating onset of hydrolysis. As shown in Table I, substitution of one of the tertiary alkyl groups by other groups such as methyl, isobutyl or sec-butyl results in marked decrease in hydrolytic stability.

The hydrolytic stability data for three commercial processing stabilizers is given in Table II. The data show the extreme sensitivity of distearylpentaerythritol diphosphite to moisture. Tris(2,4-di-t-butylphenyl) phosphite is as hydrolytically stable as the phosphites of the present invention but it has a very high melting point (180°-188° C.) and requires specialized handling in the manufacturing process, such as filtration of a dispersion or crystallization from a solvent. Such compounds cannot be flaked, resulting in environmental hazard from dusting during handling operations.

The phosphites of the present invention have melting points in a 60°-100° C. range which is very convenient for flaking or, if desired, grinding operations in any manufacturing process, yet, the melting points are high enough to prevent fusion of flake or powder on storage, and their relatively high molecular weight reduces loss at high temperatures usually encountered during processing of polymers into finished products.

As shown in Table II, tris(2,4-di-t-butylphenyl)phosphite possesses the hydrolytic stability of the phosphites of the present invention but it is considerably less effective as an antioxidant. In a typical test such as ASTM 1238 Condition L, which measures the breakdown of the resin as shown by the increase in Melt Viscosity Index after each extrusion at 260° C., tris(2,4-di-t-butylphenyl) phosphite failed after three extrusions, whereas a phosphite of the present invention prepared according to Example I below did not fail after the five extrusions prescribed by the test. In the same test, distearylpentaerythritol diphosphite failed after two extrusions. The test data are given in Example IX and clearly demonstrate the unexpected superiority of the stabilizers of this invention.

TABLE I

HYDROLYTIC STABILITY OF THE PHOSPHITES*
OF THE PRESENT INVENTION AT 25° C.

| $R^1$ | $R^2$ | $R^3$ | Time to reach pH of ca. 4, Hrs. |
|---|---|---|---|
| t-Butyl | Methyl | H | 0.5 |
| t-Butyl | Isopropyl | H | 8 but less than 12 |
| t-Butyl | Sec-butyl | H | 8 but less than 12 |
| t-Butyl | t-butyl | H | greater than 24.0 |
| t-Butyl | t-butyl | t-butyl | greater than 24.0 |
| t-Butyl | Iso-amyl | Iso-amyl | greater than 24.0 |

*Compounds based on disubstituted hydroquinone.

TABLE II

HYDROLYIC STABILITY OF
COMMERCIAL PHOSPHITES AT 25° C.

| Phosphite | Time to reach pH of ca. 4 |
|---|---|
| Distearylpentaerythritol diphosphite | 5 minutes |
| Bis(2,4-di-t-butylphenyl)- pentaerythritol diphosphite | 30 minutes |
| Tris(2,4-di-t-butylphenyl) | |

TABLE II-continued

HYDROLYIC STABILITY OF
COMMERCIAL PHOSPHITES AT 25° C.

| Phosphite | Time to reach pH of ca. 4 |
|---|---|
| phosphite | 24 hours |

The compounds of the present invention are useful in stabilizing organic materials normally subject to oxidative degradation especially while being processed. Materials that are thus stabilized include a multitude of synthetic polymers. Among those polymers are various polyolefins such as polyethylene, polypropylene, polybutylene, polybutadiene, polymethylpentene. Other polymers stabilized by the compounds of the present invention include acetal resins, polyacrylates, polymethacrylates, polydialkylphthalate, cellulosics, polyamides, polyesters, polyurethanes, polycarbonate, polystyrene, polyvinyl chloride, polyvinylidene chloride. Copolymers can also be stabilized by the compounds of the present invention. Representative copolymers include ethylene/propylene copolymers, butadiene/styrene copolymers, ethylene/vinyl acetate copolymers, and ethylene/ethyl acrylate copolymers. Copolymers also include terpolymers such as ethylene/propylene/-non-conjugated diene terpolymers and acrylonitrile/-butadiene/styrene interpolymers. Polymer blends such as polystyrene/polyphenylene oxide and ethylenepropylene copolymer or terpolymer/polypropylene can also be stabilized by the compounds of the present invention. Other materials stabilized by compounds of the present invention include hot melt adhesives such as those based on polyesters, polyamides or ethylene/vinyl acetate.

For the purpose of stabilizing polymers the phosphites of this invention are used at from 0.01 or less to 1.0 or more parts, usually from 0.05 to 0.2 part per 100 parts of polymer by weight. Diphosphites of the invention are particularly effective antioxidants for polypropylene and polyethylene.

The novel phosphites of this invention are prepared by reacting first a 2,5-disubstituted 1,4-hydroquinone or 4,6-disubstituted resorcinol with excess $PCl_3$. Heating this mixture at 60°–80° C. for about five to ten hours (with evolution of HCl) provides the corresponding bis-phosphorodichloridite intermediate. Upon removal of excess $PCl_3$ by distillation, the intermediate is reacted with at least four equivalents of an appropriate phenol. The second step is carried out in presence of an HCl scavenger such as a tertiary amine and in an inert solvent at temperatures ranging from 40°–200° C. for from five to ten hours, depending on the temperature of the reaction. The resulting amine hydrochloride is then separated by filtration and the reaction solution is washed with water. The solvent and residual excess phenol is then removed by distillation. Normally vacuum is required to remove the residual phenol. The product which is in the molten state at the end of the distillation is easily transferred out of the reactor vessel. The product quickly solidifies on cooling. Thus, it can be readily processed through the finishing line into powder or, especially, flake form.

Any tertiary amine which does not react with the phenol and bis-phosphorodichloridite can be employed. Preferably lower boiling amines are used since any excess amine can be more readily removed from the product during distillation. Commercially, amines which are insoluble in water are preferred as they can be readily recovered via neutralization of the hydrochloride in aqueous base and recycled.

Any solvent is suitable provided it is inert to the reactants, immiscible with water, and is able to solubilize the product. Solvents such as dichloroethane, toluene, and xylene are preferred for purposes of the invention.

Preferred compounds of the invention are those of the above formula wherein $R^1$ and $R^2$ are independently $C_4$ to $C_8$ tertiary alkyl, and $R^3$ is hydrogen or $C_1$ to $C_8$ alkyl.

The following examples will serve to illustrate the practice of the inventions in more detail.

EXAMPLE I

Tetrakis(2,4-di-t-butylphenyl)-1,4-(2,5-di-t-butylphenylene) diphosphite.

| Charge | | |
|---|---|---|
| 2,5-di-t-butylhydroquinone | 55.6 g | 0.25 mole |
| $PCl_3$ | 137.0 g | 1.00 mole |
| Triethylamine | 120.0 g | 1.20 mole |
| 2,4-di-t-butylphenol | 288.8 g | 1.40 mole |
| Toluene | 550 ml | |

$PCl_3$ and 2,5-di-t-butylhydroquinone are placed into a 3-necked, 500 ml flask fitted with an agitator, a thermometer, and a HCl gas trap. The mixture is heated for about 7 hours at around 70° C. at which time the reaction is normally completed as indicated by the absence of the OH band in the infrared spectrum of the reaction solution. The reaction flask is then adapted for distillation. The resulting solution is heated gradually above 70° C. to remove excess $PCl_3$, which distills out of the reaction flask. The contents of the flask are heated to 150° C. at which time all excess $PCl_3$ is removed. The residue, a bisphosphorodichloridite, crystallizes when cooled to room temperature. This intermediate is dissolved in toluene (150–200 ml) and then added dropwise with stirring to a 1-liter, 3-necked flask equipped with an agitator and a thermometer, and containing triethylamine and 2,4-di-t-butylphenol in toluene solution. The mixture is heated to about 80° C. and stirred at this temperature for 5 hours. Triethylamine hydrochloride, which formed during the reaction, is separated by filtration. The filtrate is then washed with water and distilled under 10–20 mm Hg pressure, and 100° C. pot temperature to remove toluene. The residue is then distilled under 1–2 mm Hg pressure to remove excess 2,4-di-t-butylphenol. The distillation is stopped when the pot temperature reaches 180°–190° C. at which point essentially all 2,4-di-t-butylphenol is removed. The distillation residue is the product. The light amber resin, having a melting range of 75°–90° C., can be readily flaked or ground to a white powder.

Infrared and NMR analysis are consistent with the structure. Gel permeation chromatography data show the product to have a molecular weight of around 1,000 in essential agreement with the calculated value of 1,102. The phosphorus analysis is 5.20% in good agreement with the calculated value of 5.63%.

EXAMPLE II

Tetrakis(2,4-di-t-butylphenyl)-1,3-(4,6-di-t-butylphenylene)diphosphite.

| Charge | | |
|---|---|---|
| 4,6-di-t-butylresorcinol | 55.6 g | 0.25 mole |
| PCl₃ | 137.0 g | 1.00 mole |
| 2,4-di-t-butylphenol | 250.0 g | 1.20 mole |
| Triethylamine | 120.0 g | 1.20 mole |
| Toluene | 550.0 ml | |

The procedure of Example I was repeated, giving the product as a light amber resin, having a 77°–92° C. melting range. The resin is easily flaked or ground to a white powder. Infrared and NMR analysis are consistent with the structure. Gel permeation chromotography data show the product to have a molecular weight of around 1,000 essentially in agreement with the calculated value of 1,102. The phosphorus analysis was 5.60% in agreement with the calculated value of 5.63%.

EXAMPLE III

Tetrakis(2,4-di-t-butylphenyl)-1,4-(2,5-di-t-amylphenylene) diphosphite.

| Charge | | |
|---|---|---|
| PCl₃ | 205.0 g | 1.50 moles |
| 2,5-di-t-amylhydroquinone | 62.5 g | 0.25 mole |
| 2,5-di-t-butylphenol | 216.0 g | 1.0 mole |
| Triethylamine | 120.0 g | 1.20 moles |
| Toluene | 550 ml | |

The procedure of Example I was repeated, giving the product as an amber resin, having a melting range of 75°–80° C. The resin is easily flaked or ground to a white powder. Infrared and NMR analysis are consistent with the structure. Gel permeation chromotography data show the product to have a molecular weight of around 1,000, essentially in agreement with the calculated value of 1,130. The phosphorus analysis was 5.45% in good agreement with the calculated value of 5.49%.

EXAMPLE IV

Tetrakis(2,4-di-t-butylphenyl)-1,4-[2,5-bis(1,1,3,3-tetramethylbutyl)phenylene] diphosphite.

| | | |
|---|---|---|
| 2,5-bis(1,1,3,3-tetramethylbutyl) hydroquinone | 40.7 g | 0.12 mole |
| PCl₃ | 65.7 g | 0.48 mole |
| 2,4-di-t-butylphenol | 138.6 g | 0.67 mole |
| Triethylamine | 57.0 g | 0.57 mole |
| Toluene | 550 ml | |

The procedure of Example I was repeated producing a light amber resin, having an 80°–90° C. melting range. Infrared and NMR analysis are consistent with the structure. Gel permeation chromatography data show the product to have a molecular weight of around 1,000 essentially in agreement with the calculated value of 1,184. The phosphorus analysis was 5.40% in good agreement with the calculated value of 5.24%.

EXAMPLE V

Tetrakis(2-t-butylphenyl)-1,4-(2,5-di-t-butylphenylene) diphosphite.

| Charge | | |
|---|---|---|
| 2,5-di-t-butylhydroquinone | 55.6 g | 0.25 mole |
| PCl₃ | 137.0 g | 1.00 mole |
| 2-t-butylphenol | 180.2 g | 1.20 mole |
| Triethylamine | 120.0 g | 1.20 mole |
| Toluene | 550 ml | |

The procedure of Example I was repeated. The resultant product is an amber colored resin, having a melting range of 60°–65° C. The resin can be easily flaked or ground to a white powder. Infrared and NMR analysis are consistent with the strucature. The phosphorus analysis was 6.82% and is in agreement with the calculated value of 7.06%.

EXAMPLE VI

Tetrakis[2,4-di(1,1,3,3,5,5-hexamethylhexylphenyl)]-1,4-bis [2,5-bis(alpha, alpha-dimethylbenzylphenylene)] diphosphite.

Using the general procedure mentioned above, PCL₃ is reacted with 2,5-bis(alpha, alpha-dimethylbenzylhydroquinone) at a 4/1 molar ratio. The intermediate phosphorochloridite is subsequently treated with 2,4-bis(1,1,3,3,5,5-hexamethylhexyl) phenol in presence of triethylamine and toluene leading to the above indicated diphosphite.

This compound has similar hydrolytic stability as well as antioxidative characteristics when used as in Example IX.

EXAMPLE VII

Tetrakis[2,4-bis(1,1,3-trimethylhexylphenyl)]-1,3-bis(4,5-di-t-butylphenylene) diphosphite.

To 1.0 mole of PCl₃ is added 0.25 mole of 4,6-di-t-butylresorcinol essentially according to the procedure of example I. The resultant phosphorochloridite intermediate is further reacted with 2,4-bis(1,3-trimethylhexyl)phenol to produce the above mentioned antioxidant which exhibits stabilizing properties when subjugated to example IX conditions. It also is hydrolytically stable.

EXAMPLE VIII

Tetrakis[2,(1,1-dimethylhexadecyl)-4-benzyl]-1,4-bis(2,5-di-t-butylphenylene) diphosphite.

Following essentially the procedure of Example I, 2,5-di-t-butylhydroquinone is treated with PCl₃ producing the corresponding substituted phospohorchloridite, which in turn is reacted with 2-(1,1-dimethylhexadecyl)phenol. The resultant product mentioned above has a hydrolytic stability and provides protection against deterioration of organic polymers.

EXAMPLE IX

This example describes the utility of the diphosphites of general formula as processing aids/antioxidants in polypropylene. For comparison, two commercial phosphite stabilizers for polyolefin were included in the test. The phosphites were compounded in a Banbury (trademark) mixer into Profax 6501 (trademark), a polypropylene resin. Melt flow readings were made after the Banbury mixing step and used as the initial melt indexes. The resin was then chopped and extruded at 260° C. for five passes. After each pass, melt index was determined according to ASTM 1238, Condition L.

| MELT INDEX ASTM 1238 | | | | | | |
|---|---|---|---|---|---|---|
| Phosphite Processing | | No. of Passes | | | | |
| Aid (0.1%) | Initial | 1 | 2 | 3 | 4 | 5 |
| (1) Distearylpentaery-thritol diphosphite | 2.9 | 6.3 | * | | | |
| (2) Tris(2,4-di-t-butyl-phenyl) phosphite | 3.4 | 6.9 | 9.8 | * | | |
| (3) Phosphite from Example I | 2.3 | 3.3 | 4.9 | 5.7 | 6.2 | 8.4 |

*Melt index too high to measure

The results clearly demonstrate the superior efficacy of the compound of this invention (3) over known materials (1 & 2) with respect to plasticizing and stabilizing effects.

What is claimed is:

1. A diphosphite having the structural formula

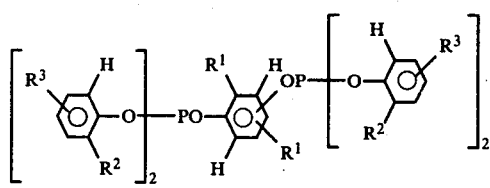

wherein $R^1$ and $R^2$ may be the same or different and are $C_4$ to $C_{12}$ tertiary alkyl or $C_9$ to $C_{14}$ tertiary aralkyl; $R^3$ is hydrogen, $C_1$ to $C_{18}$ alkyl or $C_7$ to $C_{18}$ aralkyl.

2. The compound of claim 1 based on 2,5-disubstituted hydroquinone, the said substituents being $R^1$ as defined in claim 1.

3. The compound of claim 1 based on 4,6-disubstituted resorcinol, the said substituents being $R^1$ as defined in claim 1.

4. The compound of claim 1, 2 or 3 wherein $R^1$ and $R^2$ are independently $C_4$ to $C_8$ tertiary alkyl, and $R^3$ is hydrogen or $C_1$ to $C_8$ alkyl.

5. The compound of claim 1 which is tetrakis(2,4-di-t-butylphenyl)-1,4-(2,5-di-t-butylphenylene) diphosphite.

6. The compound of claim 1 which is tetrakis(2,4-di-t-butylphenyl)-1,3-(4,6-di-t-butylphenylene) diphosphite.

7. The compound of claim 1 which is tetrakis(2,4-di-t-butylphenyl)-1,4-(2,5-di-t-amylphenylene) diphosphite.

8. The compound of claim 1 which is tetrakis(2,4-di-t-butylphenyl)-1,4-[2,5-bis(1,1,3,3-tetramethylbutyl)phenylene] diphosphite.

9. The compound of claim 1 which is tetrakis(2-t-butylphenyl)-1,4-(2,5-di-t-butylphenylene) diphosphite.

10. The compound of claim 1 which is tetrakis[2,4-di(1,1,3,3,5,5-hexamethylhexylphenyl)]-1,4-bis[2,5-bis-(alpha, alpha-dimethylbenxylphenylene)] diphosphite.

11. The compound of claim 1 which is tetrakis[2,4-bis(1,1,3-trimethylhexylphenyl)]-1,3-bis(4,5-di-t-butylphenylene) diphosphite.

12. The compound of claim 1 which is tetrakis[2-(1,1-dimethylhexadecyl)-4-benzyl]-1,4-bis(2,5-di-t-butylphenylene) diphosphite.

* * * * *